(12) United States Patent
Northcote et al.

(10) Patent No.: US 6,790,862 B2
(45) Date of Patent: Sep. 14, 2004

(54) BIOACTIVE COMPOUND

(75) Inventors: Peter T. Northcote, Wellington (NZ);
John H. Miller, Wellington (NZ);
Kylie A. Hood, Wellington (NZ);
Lyndon M. West, Wellington (NZ)

(73) Assignee: Victoria Link Limited, Wellington (NZ)

(*) Notice: Subject to any disclaimer, the term of this patent is extended or adjusted under 35 U.S.C. 154(b) by 0 days.

(21) Appl. No.: 10/071,209

(22) Filed: Feb. 11, 2002

(65) Prior Publication Data

US 2002/0193423 A1 Dec. 19, 2002

Related U.S. Application Data

(63) Continuation of application No. PCT/NZ00/00152, filed on Aug. 9, 2000.

(30) Foreign Application Priority Data

Aug. 9, 1999 (NZ) .................................................. 337159

(51) Int. Cl.[7] ............................................. A61K 31/335
(52) U.S. Cl. ...................................... 514/449; 549/510
(58) Field of Search .......................... 514/449; 549/510

(56) References Cited

PUBLICATIONS

Perry et al., J. Am. Chem. Soc., 110, 1988, pp. 4850–4851, Mycalamide A, an Antiviral Compound from a New Zealand . . . .
Northcote et al, Tetrahedron Letters, vol. 32, No. 44, 1991, pp. 6411–6414, Pateamine: A Potent Cytotoxin From The . . . .
Chemical Abstracts 2000, 132:149195, pp. 1 and 2.
West et al, J. Org. Chem., 65, 2000, pp. 445–449, Peloruside A: A Potent Cytotoxic Macrolide Isolated from the New Zealand . . . .
Hood et al, Apoptosis 6, 2001, pp. 207–219, Induction of apoptosis by the marine sponge (Mycale) metabolites . . . .
Hood et al, Anti–Cancer Drug Design, 16, 2001, pp. 155–156, The novel cytotoxic sponge metabolite peloruside A . . . .

*Primary Examiner*—Amelia A. Owens
(74) *Attorney, Agent, or Firm*—Jacobson Holman PLLC

(57) ABSTRACT

This invention relates to a bioactive compound and to compositions which contain it. The invention further relates to methods of microtubule stabilization. In particular, it relates to a compound which has cytotoxic properties and which therefore has utility in inter alia anti-tumor treatments.

20 Claims, 6 Drawing Sheets

BIOACTIVE COMPOUND

This is a continuation application of PCT/NZ00/00152, filed Aug. 9, 2000, and published in English.

This invention relates to a bioactive compound and to compositions which contain it. The invention further relates to methods of microtubule stabilization. In particular, it relates to a compound which has cytotoxic properties and which therefore has utility in inter alia anti-tumor treatments.

BACKGROUND

In the search for anti-cancer drugs, compounds from natural sources, such as paclitaxel, extracted from the bark of the Pacific yew tree, have displayed useful anti-cancer activity and proven successful in clinical trials.

Marine sponges of the genus Mycale (Carmea) are a rich source of bioactive secondary metabolites of diverse structures. The mycalysines, mycalolides, deoxytedanolide and the macrolide pateamine have all been isolated from members of this genus and exhibit a variety of properties, including cytotoxic properties. See, for example, Perry et al., *J. Am. Chem. Soc.* (1988), 110, 4850–4851 and Northcote et al., *Tetrahedron Letters* (1991) 32, 6411–6414.

The strategy of using tubulin as a target for cancer chemotherapy is based on the increased growth and division of cancer cells and the fact that drugs that interfere with mitosis such as the vinca alkaloids that depolymerize microtubules have proven effective in the treatment of cancer. Paclitaxel (Taxol®) and taxotere (Docetaxel®) target tubulin but, unlike the vinca alkaloids and colchicine, cause polymerization and stabilization of microtubules. Both are currently used therapeutically for the treatment of solid tumors of the breast, ovary, and lung (He L., Orr G. A., Horwitz S. B., *Drug Discovery Today* (2001), 6, 1153–1164). Microtubule-stabilizing compounds can be divided into three groups:

(a) diterpenes, including the taxanes, paclitaxel and taxotere, isolated from Yew trees (He L. et al.) and eleutherobin/sarcodictyin, isolated from marine corals (Long B. H., Carboni J. M., Wasserman A. J., Cornell L. A., Casazza A. M., Jensen P. R., Lindel T., Fenical W., Fairchild C. R., *Cancer Res.* (1998), 58, 1111–1115);

(b) macrolides, including epothilones, isolated from the bacterium *Sorangium cellulosum* (Bollag D. M., McQueney P. A., Zhu J., Hensens O., Koupal L., Liesch J., Goetz M., Lazarides E., Woods C. M., *Cancer Res.* (1995), 55, 2325–2333 and Kowalski R. J., Giannakakou P., Hamel E., *J. Biol. Chem.* (1997), 272, 2534–2541) and laulimalides, isolated from the marine sponge *Cacospongia mycofijiensis* (Mooberry S. L., Tien G., Hernandez A. H., Plubrukarn A., Davidson B. S., *Cancer Res.* (1999), 59 653–660); and (c) polyhydroxylated alkatetraene lactones, including discodermolide, isolated from a Caribbean sponge (Ter Haar E., Kowalski R. J., Hamel E., Lin C. M., Longley R. E., Gunasekera S. P., Rosenkranz H. S., Day B. W., *Biochem.* (1996), 35, 243–250 and Kowalski R. J., Giannakakou P., Gunasekera P., Longley R. E., Day B. W., Hamel E., *Molec. Pharmacol.* (1997), 52, 613–622).

The complex chemical syntheses required to produce clinically useful amounts of such drugs has limited their development as anti-cancer agents, although both epothilone and the more complex paclitaxel and taxotere have now been synthesized in sufficient amounts for clinical use. In addition, paclitaxel is lipophilic, thus having low aqueous solubility, and for clinical use, it must be dissolved in Cremaphor/ethanol, a vehicle that contributes to paclitaxel's undesirable side effects that include hypersensitivity reactions, neutropenia, peripheral neuropathy, and alopecia (Bollag D. M. et al.). Paclitaxel's hydrophobicity also promotes the acquisition of the multiple drug resistance (MDR) phenotype through expression of P-glycoprotein (P-gp) (Parekh H., Wiesen K., Simpkins H., *Biochem. Pharmacol.* (1997), 53, 461–470). P-gp is responsible for the efflux of a broad range of organic solutes from the cell, and paclitaxel is just one of these. In addition toover-expression of P-gp, some cells become resistant as a result of mutation of the paclitaxel binding site on β-tubulin (Giannakakou P., Gussio R., Nogales E., Downing K. H., Zaharevitz D., Bollbuck B., Poy G., Sackett D., Nicolaou K. C., Fojo T., *Proc. Nat. Acad. Sci.* (USA) (2000), 97, 2904–2909).

Therefore there is a need for other microtubule-stabilizers with similar anti-mitotic activity to paclitaxel but which lack the interaction with P-gp or which bind to unique sites on the tubulin polymer. Epothilones, laulimalides, and discodermolides have shown promise in this area, displaying less loss of toxicity to certain P-gp-expressing cells than paclitaxel (Bollag D. M. et al., Kowalski R. J. et al., Mooberry S. L. et al. and Kowalski R. J. et al.), although still being transported to some extent by P-gp. At least three of the known microtubule-stabilizing drugs, the epothilones (Bollag D. M. et al. and Kowalski R. J. et al.), discodermolide (Kowalski R. J. et al.), and the eleutherobins (Long B. H.), compete with [$^3$H]-paclitaxel for its binding site on β-tubulin; however, epothilone and discodermolide also show different sensitivities to particular β-tubulin mutations despite binding to a similar site. The paclitaxel binding site of β-tubulin is available at 3.5 Å resolution (Nogales E. et al.), facilitating drug modeling approaches. A common pharmacophore has been partially described, but further structure/function studies are needed (He L. et al., Giannakakou P. et al., He L., Jagtap P. G., Kingston D. G. I., Shen H-J., Orr G. A., Horwitz S. B., Biochem. (2000), 39, 3972–3978 and Nicolaou K. C., Ritzén A., Namoto K., *Chem. Comm.* (2001), 17, 1523–1535).

Recent in vivo tests on tumor formation in nude mice have shown promise for desoxyepothilone analogues, specifically Z-12,13-desoxyepothilone B (dEpoB) and its more water soluble analogue, dEpoF (Chou T.-C., O'Conner O. A., Tong W. P., Guan Y., Zhang Z.-G., Stachel S. J., Lee C., Danishefsky S. J., *Proc. Natl. Acad. Sci.* (USA) (2001), 98, 8113–8118). Interestingly, the parent compound, epothilone B, although more potent than dEpoB or dEpoF, is too cytotoxic in vivo for use as an anti-cancer drug.

The applicants have now identified a bioactive compound from a marine sponge of the genus Mycale. The applicants have established the compound as a novel microtubule-stabilizing agent with potentially unique properties to the other known microtubule-stabilizing drugs. It is towards this compound, which the applicants have termed Peloruside A, to its functionally equivalent analogues, and to compositions, uses and methods of treatment which employ these compounds, that the present invention is broadly directed.

SUMMARY OF THE INVENTION

In a first aspect, the invention therefore provides a compound of formula (I);

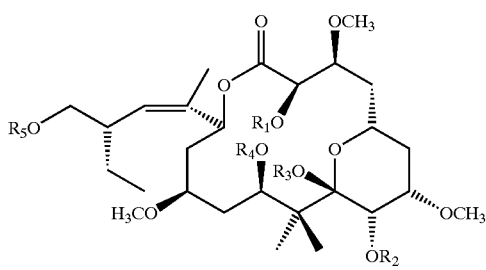

(I)

wherein $R_1$, $R_2$, $R_3$, $R_4$ and $R_5$ are independently hydrogen, alkyl or acyl; or a functionally equivalent analogue thereof.

In a further aspect, the invention provides a compound of formula (II);

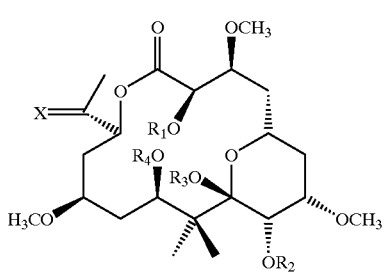

(II)

wherein X is O or $=C(R_5)R_6$ and $R_1$, $R_2$, $R_3$, $R_4$, $R_5$, and $R_6$ are independently hydrogen, alkyl or acyl; or a functionally equivalent analogue thereof.

Preferably, the compound is of formula (III);

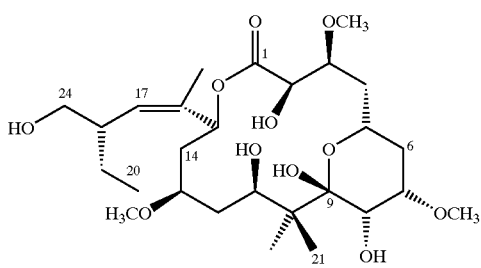

(III)

or a functionally equivalent analogue thereof.

In another aspect, the invention provides a compound of formula (IV);

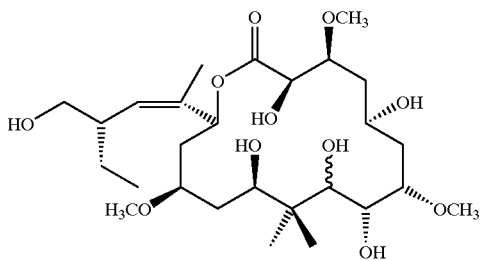

(IV)

or a functionally equivalent analogue thereof.

In another aspect, the invention provides a bioactive compound which has the NMR and/or IR spectral signature of FIGS. 1 and 2.

In another aspect, the invention provides composition which comprises a compound of the invention together with a suitable carrier therefor.

Preferably, the composition is a pharmaceutical composition.

In another further aspect, the invention provides a method of prophylaxis or therapy which comprises the step of administering to a patient in need of the same a compound or a composition of the invention.

Preferably, the prophylaxis or therapy is achieved by inhibiting the proliferation of cells.

Preferably, the compound is administered in an amount effective to provide microtubule stabilization.

A preferred method is a treatment of a patient against cancer.

The above formulae specify relative stereochemistry only.

DESCRIPTION OF THE DRAWINGS

While the invention is broadly as described above, it will also be appreciated that it is not limited thereto but also includes embodiments of which the following description provides examples. In particular, a better understanding of the present invention will be gained through reference to the accompanying drawings in which.

DESCRIPTION OF THE INVENTION

Figure 1:
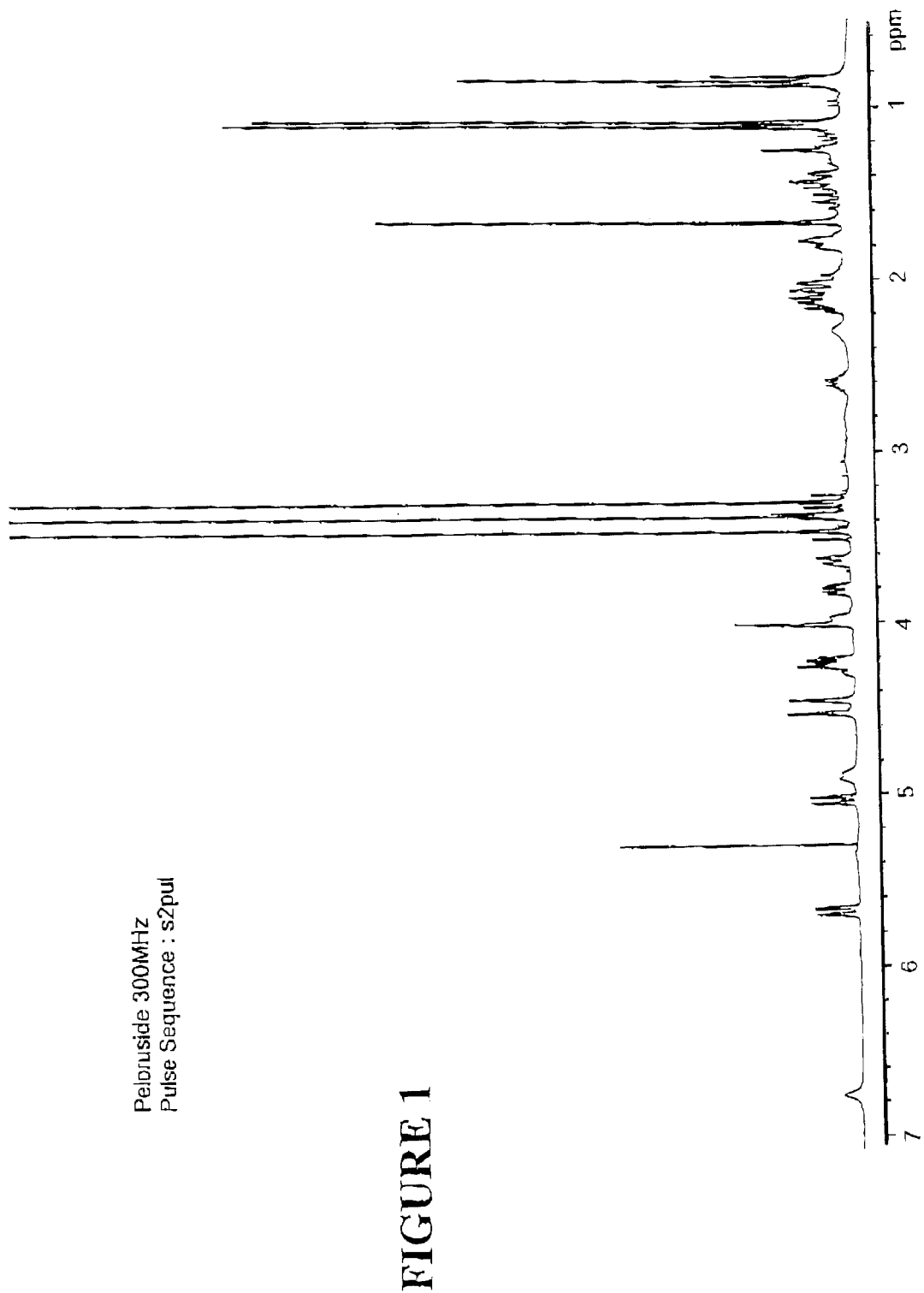
FIG. 1 shows the $^1$H NMR spectral signature for Peloruside A.

As described above, the present invention has as its primary focus a new bioactive compound and its functionally equivalent analogues. This compound has been isolated from a marine sponge of the genus Mycale from Pelorus Sound, New Zealand. It has also been found, inter alia, to have cytotoxic properties; hence the name Peloruside A.

The compound of the invention can be isolated from marine sponges obtained from New Zealand coastal waters (including Pelorus Sound, HalfMoon Bay, Stewart Island and Kapiti). The sponges are a species which belongs to the genus Mycale (Family Mycalidae, Order Poecilosclerida). Individuals of this species may be encrusting or massive, with a chocolate brown ectosome, often with a purple tinge. The sponge surface often has large oscules (2–4 mm diameter) and may appear stippled due to the presence of polychaete worm tubes. The choanosome is light brown with a reticulate skeleton composed of tracts of subtylostyles (220–270 mm long) interspersed with microscleres: anisochelae of 2 size classes, 18–20 and 26–30 mm; sigmas, 20–26 mm; and raphides. The skeleton at ectosome consists of spicules identical to the choanosome, but tangentially arranged and supported by erect spicule brushes.

Sponge specimens which contain Peloruside A can be readily collected manually, generally at depths of 3 to 20 meters, during the winter months.

Such sponges can be farmed commercially should this provide desirable.

A variety of methods can be used to isolate and purify Peloruside A from samples of Mycale, including solvent extraction, partition chromatography, silica gel chromatography, liquid-liquid distribution in a Craig apparatus, adsorption on resins, and crystallization from solvents.

The isolation and purification methods chosen can be monitored at each step by performing in vitro and/or in vivo antitumor tests as described by Geran R. I., Greenberg N. H., MacDonald M. M., Schumacher A. M. and Abbott B. S. in *Cancer Chemother. Rep.* (1972), Part 3, 3 (2), 1–103, and by Schmidt J. M. and Pettit G. R., in *Experientia* (1978), 34, 659–660. Such tests include the determination of the concentration of active material required to inhibit the growth of tumor cells in culture (eg. the concentration required to inhibit growth by 50 percent or the $E.D._{.50}$) and of the dose of active material required to prolong the life of mice bearing transplanted tumors.

A preferred extraction process is described in the examples.

Peloruside A has the structure set out in formula (III) above. However, analogues and/or structural variants of Peloruside A which retain substantially equivalent bioactivity to Peloruside A also form part of the invention. For example, any of the accessible OH groups shown in the formulae can be replaced with, for example, alkyl groups provided that the poly-oxygenation of the subject molecule overall is not significantly reduced. Equally, the methoxy groups can be replaced with OH groups or longer chain alkoxy groups.

The selection of substituent groups and the processes by which their substitution can be achieved will be a matter of routine choice for the skilled worker in this field.

Further variations target the alkene side chain, with the length of the chain being altered.

The alkene side chain present in the compounds of formula (I) may be derivatized to prepare compounds of formula (II). By the use of ozonolysis or other suitable techniques known to persons skilled in the art, the alkene carbon-carbon double bond may be cleaved to give the methyl ketone represented by formula (II), wherein 'X is O. This methyl ketone may be derivatized by the use of the Wittig reaction, or other suitable synthetic reaction such as are well-known to those skilled in the art, to give the compounds represented by formula (II), wherein X is =$C(R_5)R_6$, wherein $R_5$ and $R_6$ are independently hydrogen, alkyl or acyl.

Analogues within the scope of the invention will retain the macrolide structure, inclusive of the pyranose ring and gem-dimethyls as shown in Formula (III).

The fact that Peloruside A has free hydroxyl groups also means that acyl esters can be prepared. Such acyl esters of Peloruside A can be prepared by methods well known to those skilled in the art. Acyl derivatives of Peloruside A can be used for the same biological purposes as the parent compound.

Acids which can be used in the acylation of Peloruside A to form compounds of formula (I) include:

(d) saturated or unsaturated, straight or branched chain aliphatic carboxylic acids, for example, acetic, propionic, butyric, isobutyric, tert-butylacetic, valeric, isovaleric, caproic, caprylic, decanoic, dodecanoic, lauric, tridecanoic, myristic, pentadecanoic, palmitic, margaric, stearic, acrylic, crotonic, undecylenic, oleic, hexynoic, heptynoic or octynoic acid;

(e) saturated or unsaturated, alicyclic carboxylic acids, for example, cyclobutanecarboxylic acid, cyclopentanecarboxylic acid, cyclopentenecarboxylic acid, methylcyclopentenecarboxylic acid, cyclohexanecarboxylic acid, dimethylcyclohexanecarboxylic acid or dipropylcyclohexanecarboxylic acid;

(f) saturated or unsaturated, alicyclic aliphatic carboxylic acids, for example, cyclopentaneacetic acid, cyclopentanepropionic acid, cyclohexaneacetic acid, cyclohexanebutyric acid or methylcyclohexaneacetic acid;

(g) aromatic carboxylic acids, for example, benzoic acid, toluic acid, naphthoic acid, ethylbenzoic acid, isobutylbenzoic acid or methylbutylbenzoic acid; and (h) aromatic-aliphatic carboxylic acids, for example, phenylacetic acid, phenylpropionic acid, phenylvaleric acid, cinnamic acid, phenylpropiolic acid and naphthylacetic acid, and the like.

Suitable halo-, nitro-, hydroxy-, keto-, amino-, cyano-, thiocyano-, and lower alkoxyhydrocarbon carboxylic acids include hydrocarboncarboxylic acids as given above which are substituted by one or more of halogen, nitro, hydroxy, keto, amino, cyano, or thiocyano, or lower alkoxy, advantageously lower alkoxy of not more than six carbon atoms, for example, methoxy, ethoxy, propoxy, butoxy, amyloxy, hexyloxy, and isomeric forms thereof.

As described below, Peloruside A has been determined to have cytotoxic properties in tests which are predictive of cytotoxic (including anti-tumor) activity in mammals, including humans. The applicants have further determined that like paclitaxel, Peloruside A arrests cells in the $G_2/M$ phase of the cell cycle and induces apoptosis.

Such properties therefore render Peloruside A suitable for use, alone or together with other active agents, in a number of therapeutic applications, including in anti-tumor treatments. In addition, the relatively simple structure of Peloruside A makes it suitable for the design and synthesis of analogues with improved tumor targeting and reduced tumor cross-resistance.

The administration of Peloruside A is particularly useful for treating animals or humans bearing a neoplastic disease, for example, acute myelocytic leukemia, acute lymphocytic leukemia, malignant melanoma, adenocarcinoma of the lung, neuroblastoma, small cell carcinoma of the lung, breast carcinoma, colon carcinoma, ovarian carcinoma, bladder carcinoma, and the like.

The dosage administered will be dependent upon the identity of the neoplastic disease, the type of host involved, age, health, weight, kind of concurrent treatment, if any, frequency of treatment and therapeutic ratio.

Illustratively, dosage levels of the administered active ingredients can be: intravenous, 0.1 to about 200 mg/kg; intraperitoneal, 1 to about 500 mg/kg; subcutaneous, 1 to about 500 mg/kg; intramuscular, 1 to about 500 mg/kg; orally, 5 to about 1000 mg/kg; intranasal instillation, 5 to about 1000 mg/kg; and aerosol, 5 to about 1000 mg/kg of animal (body) weight.

Expressed in terms of concentration, an active ingredient can be present in the compositions of the present invention for localized use about the cutis, intranasally, pharyngolaryngeally, bronchially, broncholially, intravaginally, rectally, or ocularly in a concentration of from about 0.01 to about 50% w/w of the composition; preferably about 1 to about 20% w/w of the composition; and for parenteral use in a concentration of from about 0.05 to about 50% w/v of the composition and preferably from about 5 to about 20% w/v.

The compositions of the present invention are preferably presented for administration to humans and animals in unit dosage forms, such as tablets, capsules, pills, powders, granules, suppositories, sterile parenteral solutions or suspensions, sterile non-parenteral solutions or suspensions, and oral solutions or suspensions and the like, containing suitable quantities of an active ingredient.

For oral administration either solid or fluid unit dosage forms can be prepared.

Powders are prepared quite simply by comminuting the active ingredient to a suitably fine size and mixing with a similarly comminuted diluent. The diluent can be an edible carbohydrate material such as lactose or starch. Advantageously, a sweetening agent or sugar is present as well as a flavouring oil.

Capsules are produced by preparing a powder mixture as hereinbefore described and filling into formed gelatin sheaths. Advantageously, as an adjuvant to the filling operation, a lubricant such as a talc, magnesium stearate, calcium stearate and the like is added to the powder mixture before the filing operation.

Soft gelatin capsules are prepared by machine encapsulation of a slurry of active ingredients with an acceptable vegetable oil, light liquid petrolatum or other inert oil or triglyceride.

Tablets are made by preparing a powder mixture, granulating or slugging, adding a lubricant and pressing into tablets. The powder mixture is prepared by mixing an active ingredient, suitably comminuted, with a diluent or base such as starch, lactose, kaolin, dicalcium phosphate and the like. The powder mixture can be granulated by wetting with a binder such as corn syrup, gelatin solution, methylcellulose solution or acacia mucilage and forcing through a screen. As an alternative to granulating, the powder mixture can be slugged, i.e., run through the tablet machine and the resulting imperfectly formed tablets broken into pieces (slugs). The slugs can be lubricated to prevent sticking to the tablet-forming dies by means of the addition of stearic acid, a stearic salt, talc or mineral oil. The lubricated mixture is then compressed into tablets.

Advantageously the tablet can be provided with a protective coating consisting of a sealing coat or enteric coat of shellac, a coating of sugar and methylcellulose and polish coating of carnauba wax.

Fluid unit dosage forms for oral administration such as syrups, elixirs and suspensions can be prepared wherein each teaspoonful of composition contains a predetermined amount of active ingredient for administration. The water-soluble forms can be dissolved in an aqueous vehicle together with sugar, flavouring agents and preservatives to form a syrup. An elixir is prepared by using a hydroalcoholic vehicle with suitable sweeteners together with a flavouring agent. Suspensions can be prepared of the insoluble forms with a suitable vehicle with the aid of a suspending agent such as acacia, tragacanth, methylcellulose.

For parenteral administration, fluid unit dosage forms are prepared utilizing an active ingredient and a sterile vehicle with water being preferred. The active ingredient, depending on the form and concentration used, can be either suspended or dissolved in the vehicle. In preparing solutions the water-soluble active ingredient can be dissolved in water for injection and filter sterilized before filling into a suitable vial or ampoule and sealing. Advantageously, adjuvants such as a local anesthetic, preservative and buffering agents can be dissolved in the vehicle. Parenteral suspensions are prepared in substantially the same manner except that an active ingredient is suspended in the vehicle instead of being dissolved and sterilization cannot be accomplished by filtration. The active ingredient can be sterilized by exposure to ethylene oxide before suspending in the sterile vehicle. Advantageously, a surfactant or wetting agent is included in the composition to facilitate uniform distribution of the active ingredient.

In addition to oral and parenteral administration, the rectal and vaginal routes can be utilized. An active ingredient can be administered by means of a suppository. A vehicle which has a melting point at about body temperature or one that is readily soluble can be utilized. For example, cocoa butter and various polyethylene glycols (Carbowaxes) can serve as the vehicle.

For intranasal instillation, fluid unit dosage forms are prepared utilizing an active ingredient and a suitable pharmaceutical vehicle, water being preferred, or by dry powder for insufflation.

For use as aerosols the active ingredients can be packaged in a pressurized aerosol container together with a gaseous or liquefied propellant, for example, dichlorodifluoromethane, carbon dioxide, nitrogen, propane, and the like, with the usual adjuvants such as cosolvents and wetting agents, as may be necessary or desirable.

The invention will now be described with reference to the following examples. It will be appreciated that the examples are provided by way of illustration of the invention only and are not intended in any way to be limiting.

EXAMPLE ONE

Isolation and Characterization of Peloruside A

A. Isolation

Sponge specimens were collected in Pelorus Sound, South Island, New Zealand at depths of 7–15M. A single frozen specimen (170 g wet weight, NIWA # 95DBMYC 2–6) was cut into small segments and extracted with methanol (2×600 mL) for 24 hr. The second and first methanolic extracts were passed through a glass column packed with 75 mL of Supelco Diaion HP20® polystyrenedivinylbenzene beads pre-equilibrated with 50% methanol in water. The eluents were combined and passed through the same column. The resulting eluent was diluted with 150 mL of water and passed through the column. Finally the testing element was diluted with 2800 mL of water and passed back through the same column. The column was then washed with 100 mL of water and eluted with 150 mL fractions of 1) 20% acetone in water, 2) 55% acetone in water, 3) 55% acetone in 0.2 M $NH_4OH$, and 4) 55% acetone in 0.2 M $NH_4OH$ adjusted to pH 4.9 with acetic acid. Fraction 2 was diluted with 150 mL of water and passed through a glass column packed with 35 mL of HP20® pre-equilibrated with water. The column was washed with 50 mL of water and eluted with 100 mL of acetone. The acetone eluent was concentrated to dryness to yield 78.8 mg of a viscous brown oil. The resulting oil was dissolved in 25 mL of methanol and passed through a small glass column containing 250 mg of TosoHass Amberchrom®. The column eluent was diluted with 60 mL of water and passed back through the column. The column was washed with 20 mL of water and the loaded Amberchrom® was transferred on top of a 20×1.5 cm Amberchrom® column pre-equilibrated with water. The column was eluted with increasing concentrations of acetone in water in a stepped gradient fashion. The 32–34% acetone in water fractions were concentrated to dryness to yield a colourless oil (2.2 mg). The 38–40% acetone in water fractions were concentrated to dryness to yield mycalamide A (10.6 mg). The fourth fraction eluted from the original HP20 column at pH 4.0 was diluted with 150 mL of water, adjusted to pH 7.0 with $NH_3$, and passed through a glass column packed with 30 mL of HP20® pre-equilibrated with water. The column was washed with 50 mL of water and eluted with 100 mL of acetone. The acetone eluent was concentrated to dryness to yield 38 mg of a yellow oil. The oil was dissolved in 12 mL of methanol and passed through 2.5 mL of amino bonded phase packing material. The eluent was concentrated to dryness to yield 11.7 mg of pateamine.

B. Characterization of the Compound Present in 32–34% Acetone Fraction

The structure of the compound present in the 32–34% acetone fraction was determined to be as follows:

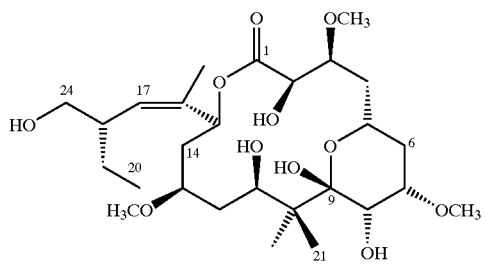

The compound has been termed Peloruside A (Formula III). The $^1H$ and $^{13}C$ NMR assignments of Peloruside A in $CDCl_3$ are summarized in Table 1 below:

TABLE 1

$^1H$ and $^{13}C$ NMR Assignments of Peloruside A in $CDCl_3$

| Position | $^{13}C$ δ (ppm) | mult | $^1H$ δ (ppm) | mult, J (Hz) |
|---|---|---|---|---|
| 1 | 173.95 | s | | |
| 2 | 70.26 | d | 4.53 | s |
| 3 | 78.27 | d | 4.22 | dd (10.5, 5.5) |
| 4a | 32.59 | t | 1.78 | M |
| 4b | | | 2.13 | m |
| 5 | 63.51 | d | 4.25 | tdd (11, 4.5, 2.5) |
| 6a | 31.65 | t | 1.53 | q (12) |
| 6b | | | 1.78 | ddd (12.5, 5.5, 2.5) |
| 7 | 75.90 | d | 3.82 | ddd (11.5, 5, 3) |
| 8 | 66.84 | d | 4.02 | d (3) |
| 9 | 101.89 | s | | |
| 10 | 43.63 | s | | |
| 11 | 73.85 | d | 4.89 | br d (10) |
| 12a | 33.93 | t | 1.40 | d (14.5) |
| 12b | | | 2.07 | ddd (15, 11.5, 4.5) |
| 13 | 77.88 | d | 3.99 | br d (9.5) |
| 14a | 35.68 | t | 2.02 | ddd (15.5, 11.5, 1) |

TABLE 1-continued $^1H$ and $^{13}C$ NMR Assignments of Peloruside A in $CDCl_3$

| Position | $^{13}C$ δ (ppm) | mult | $^1H$ δ (ppm) | mult, J (Hz) |
|---|---|---|---|---|
| 14b | | | 2.15 | 555 (15.5, 10.5, 1) |
| 15 | 70.86 | d | 5.68 | d (10.5) |
| 16 | 136.05 | s | | |
| 17 | 131.13 | d | 5.05 | d (10) |
| 18 | 43.29 | d | 2.61 | m |
| 19a | 24.60 | t | 1.17 | m |
| 19b | | | 1.44 | m |
| 20 | 12.23 | q | 0.85 | t (7.5) |
| 21 | 15.77 | q | 1.08 | s |
| 22 | 20.77 | q | 1.12 | s |
| 23 | 17.45 | q | 1.67 | d (1) |
| 24a | 66.94 | t | 3.36 | t (10.5) |
| 24b | | | 3.64 | dd (10.5, 4) |
| 3Me | 56.09 | q | 3.31 | s |
| 7Me | 55.68 | q | 3.38 | s |
| 13Me | 59.06 | q | 3.48 | s |
| 6OH | | | 6.75 | s |

FIG. 1 shows the $^1H$ NMR spectral signature of Peloruside A (300 MHz; pulse sequence: s2pul).

Figure 2:
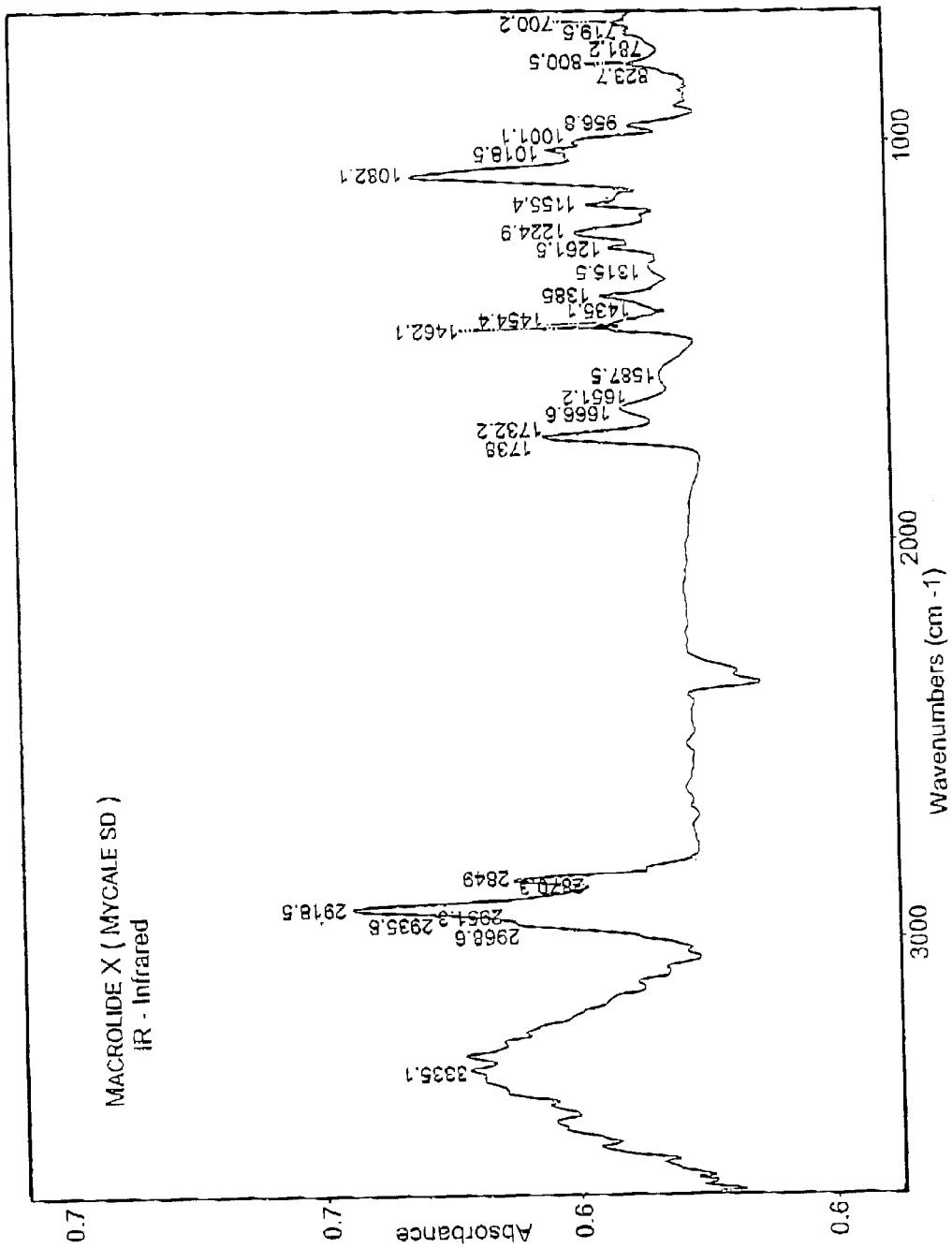
FIG. 2 shows the IR spectral signature for Peloruside A.

FIG. 2 shows the IR spectral signature of Peloruside A.

C. Bioactivity of Peloruside A

Part 1

The bioactivity of peloruside A as an anti-tumor agent was determined by an anti-tumor assay. For the anti-tumor assay a 2-fold dilution series of the same of interest is incubated for 72 hours with P388 (Murine Leukemia) cells. The concentration of sample required to reduce the P388 cell growth by 50% (comparative to control cells) is determined using the absorbance values obtained with the yellow dye MTT tetrazollum is reduced by healthy cells to the purple colour MTT formazan. The result is expressed as an $IC_{50}$ in ng/mL.

Results/Conclusion

Peloruside A was found to be cytotoxic to P388 murine leukemia cells at approximately 10 ng/mL. Although it bears some structural features of both mycalamide A (gem-dimethyls and poly-hydroxylation) and pateamine (macrolide ring), it is not closely related biochemically.

Part 2

Cytotoxicity Assays

The cytotoxicity of Peloruside A was tested in five cell lines:

LLC-PK1 (pig kidney)

H441 (human lung adenocarcinoma)

SH-SY5Y (human neuroblastoma)

P388 (murine leukemia)

32D (murine myeloid) generally in accordance with the MTT assay of Burres et al., *J. Cancer Research* (1989), 49, 2935–2940.

Briefly, cell lines were maintained in Dulbecco's modified Eagle's medium: F12 medium (50:50) (Gibco) supplemented with 10% fetal calf serum (Gibco), 100 mg/mL Penicillin G, and 50 mg/mL streptomycin sulfate. After 96 hours exposure to the toxin, cell viability was determined by the MTT calorimetric assay. MTT standard curves were determined for each cell line, and the MTT absorbance over a range of cell densities was found to be linear for each. Data were analysed with the SYSTAT statistical program using a non-linear model fit, and IC50 values were calculated using a Logit-Log plot.

The following results (expressed as $LD_{50}$ in nM) were obtained:

| Cell Line: | LD50 (nM): |
|---|---|
| P388 | 18 |
| H441 | 6.2 |
| LLC-PK1 | 3.7 |
| SH-SY5Y | 14.9 |
| 32D | 7.8 |

Additional Observations

In cell line H441, the nuclei of the cells were observed to break up into small vessicles (nuclear blebbing). This has not been observed for mycalamide A and pateamine at their respective LD50s.

In cell line SH-SY5Y no retraction of dendrites was observed which contrasts with what has been observed with mycalamide A and pateamine.

In cell line 32D the LD50 was found to increase to 1.6 mM when the cells were assayed for viability at 24 hours of exposure. This dramatic increase in LD50 has not been observed for mycalamide A, pateamine cyclohexamide.

Conclusion

These results and observations confirm Peloruside A to be a potent cytotoxin. In particular, the results of the assay conducted in relation to cancerous cell lines are predictive of anti-tumor efficacy in mammals, including humans.

EXAMPLE TWO

Activity of Peloruside A

A. Materials and Methods

Materials

Peloruside A was isolated as above and was stored at $-20°$ C. as a 1 mM solution in absolute ethanol. Paclitaxel, purified tubulin, and mouse monoclonal anti-rat b-tubulin were purchased from Sigma Chemical Co. (St. Louis, Mo.).

Preparation of the Reduction Product of Peloruside A $NaBH_4$ (2.5 mg) was added to a solution of Peloruside A (1 mg/1.5 mL MeOH). After 12 h, the reaction was quenched with $H_2O$ (4 mL) and passed through an Amberchrom column (1×2 cm). The eluent was then diluted with $H_2O$ (4 mL) and passed through the column. The eluent was diluted with $H_2O$ (8 mL) and passed through the column again. The column was eluted with $H_2O$ (4 mL) and then MeOH (3 mL). The MeOH fraction was concentrated to dryness under vacuum to give the reduction product (0.8 mg).

Less than 2% of the parent compound remained in the sample after the reduction.

Cell Culture and Cytotoxicity

Tumorigenic and non-tumorigenic cell lines were cultured as previously described in Hood K. A., West L. M., Northcote P. T., Berridge M. V., Miller J. H., *Apoptosis* (2001), 6, 207–219. These cell lines included HL-60 and KS62, two tumorigenic human myeloid leukemic cell lines, 32D clone 3 (32D), a non-tumorigenic murine myeloid cell line, 32D-ras, the ras-transformed derivative of 32D, H441, a human lung adenocarcinoma cell line, SH-SY5Y, a human neuroblastoma cell line, and LLC-PK$_1$, a non-tumorigenic pig kidney cell line. IC$_{50}$ values for Peloruside A in the different cell lines were determined using the tetrazolium-based MTT cell proliferation assay as previously described (Hood K. A et al.).

Anti-inflammatory and Metabolic Activity

The effect of Peloruside A and paclitaxel on superoxide production was determined using human peripheral blood neutrophils activated with 1 mM N-formyl-met-leu-phe (fMLP) as described previously (Tan A. S., Berridge M. V., *J. Immunol. Meth.* (2000), 238, 59–68). In this microplate assay, the cell-impermeable tetrazolium salt, WST-1, is reduced to its soluble formazan and dye reduction measured at 450 nm as an initial rate over 10–20 min. Samples were equilibrated with cells for 3 min at 37° C. and the reaction initiated by adding fMLP. Measurement of anti-metabolic activity followed a similar microplate protocol except that HeLa cells were used instead of neutrophils, cells were not activated with fMLP, and the intermediate electron acceptor, 1-methoxy phenazine methosulfate at 25 mM, was included in the WST-1 reagent to facilitate detection of low potential electrons from the plasma membrane.

Flow Cytometry

Using standard methodology, the DNA of cells was stained with propidium iodide (PI), and the proportion of cells in different phases of the cell cycle was monitored by flow cytometry. Briefly, H441 cells were treated with 1 mM Peloruside A or 1 mM paclitaxel for 24 h. Adherent cells were collected by trypsinization and added to those in suspension. The cells were then fixed with cold 70% ethanol overnight and stained with PI solution consisting of 45 mg/mL PI, 10 mg/mL RNaseA, and 0.1% glucose. After a 2 h incubation at RT, samples were analysed in a FACSort flow cytometer (Becton Dickinson).

Figure 4:
FIG. 4 shows (2A) H441 cells, (2B) Peloruside A treated H441 cells and (2C) paclitaxel treated H441 cells.
Figure 4:
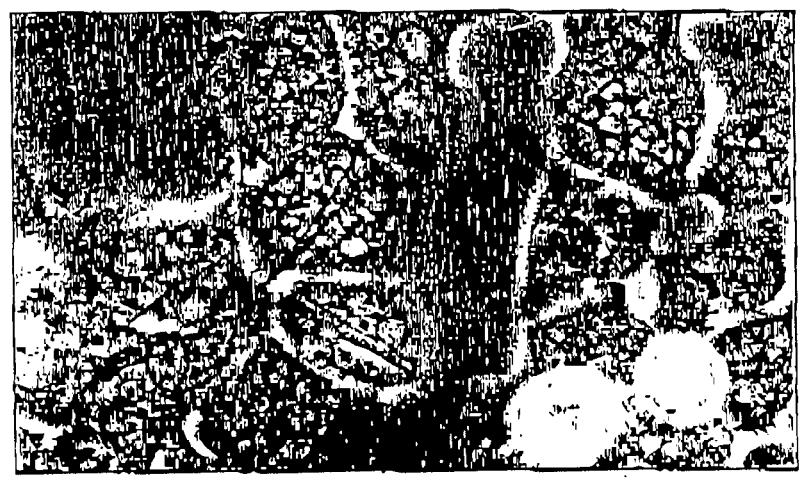
Figure 4:
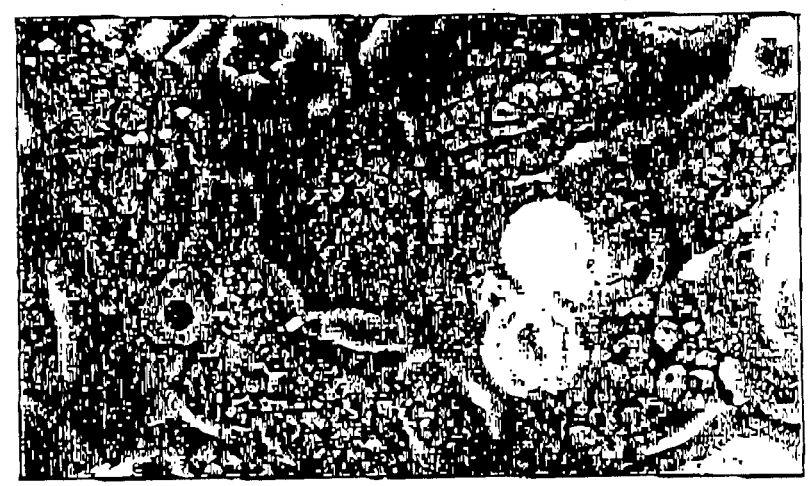

FIG. 4 shows morphological changes in H441 cells. Phase-contrast photomicrographs of H441 human lung adenocarcinoma cells: untreated control cells (A) and cells exposed for 48 h to 100 nM Peloruside A (B) or 100 nM paclitaxel (C). Note the intracellular fiber bundles in approximately 10% of the treated cells and the numerous micronuclei, each with a dark central spot of condensed DNA. Scale bar=50 mm.

Figure 5:
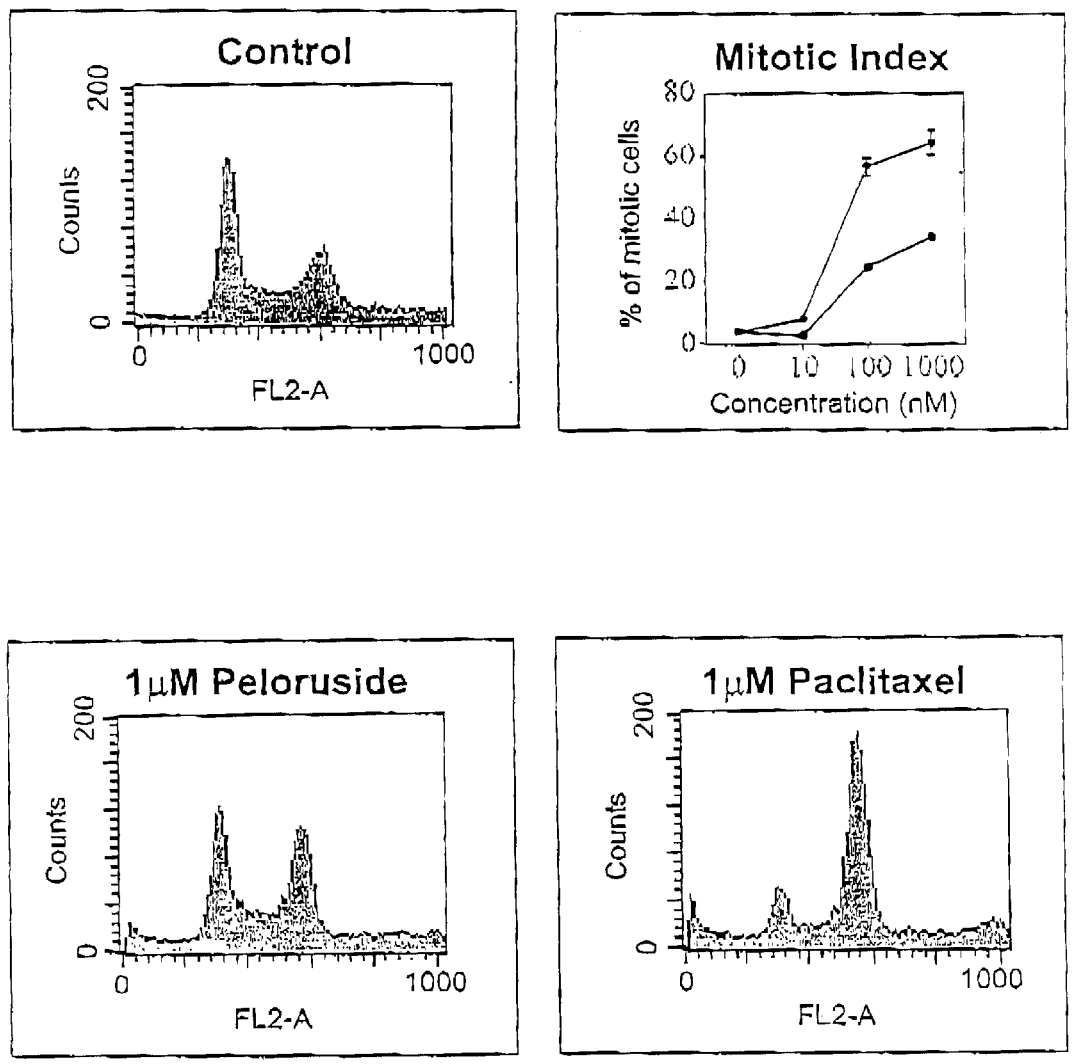
FIG. 5 shows the progression of H441 cells for a control against 1 $\mu$M Paclitaxel and 1 $\mu$M Peloruside.

FIG. 5 shows Peloruside A-induced $G_2/M$ cell cycle arrest. Cells were treated with 1 mM Peloruside A or paclitaxel, stained with PI, and counted by flow cytometry. For the mitotic index, cells were treated for 24 h with different concentrations of Peloruside A or paclitaxel, and the number of cells in mitosis divided by the total number of cells (n=at least 400 cells counted in each of 3 preparations).

In Situ Tubulin Polymerization

A simple in situ cellular assay as described by Giannakakou P., Gussio R., Nogales E., Downing K. H., Zaharevitz D., Bollbuck B., Poy G., Sackett D., Nicolaou K. C., Fojo T., *Proc. Nat. Acad. Sci.* (USA) (2000), 97, 2904–2909 was used in which the shift in tubulin from depolymerized to polymerized forms was followed by electrophoresis and Western blotting of centrifuged particulate and cytosolic fractions. To summarize, 2×10$^6$ untreated and drug-exposed HL-60 cells were lysed by exposure for 5 min at 37° C. to 100 mL of hypotonic buffer (1 mM MgCl$_2$, 2 mM EGTA, 1% Nonidet P-40, 2 mM phenylmethylsulfonyl fluoride, 1 mg/mL aprotinin, 2 mg/mL pepstatin, and 20 mM Tris-HCl, pH 6.8) and the particulate fraction separated from the soluble cytosolic fraction by high speed centrifugation for 10 min in a bench-top centrifuge. Samples labeled '0 min' received drug immediately before collection of the cells. The processing of the cells to the critical centrifugation step required approximately 30 min. The pellet was dissolved in 100 mL of sample buffer (8 M urea, 4% CHAPS, 3 M thiourea, and 40 mM DTT). Twenty mL of loading buffer was added to each 100 mL sample, the samples were vortexed and then boiled for 5 min. Twenty mL of each sample was loaded on an SDS/10% polyacrylamide gel and resolved by electrophoresis. b-Tubulin bands were identified by Western blotting using b-tubulin primary antibody (1/1000 dilution) following standard immunoblotting procedures with detection by enhanced chemiluminescence (LumiLight, Roche).

In Vitro Tubulin Polymerization and Electron Microscopy

Purified tubulin (approximately 7.5 mg protein) containing approximately 15% microtubule-associated proteins was obtained from Sigma and reconstituted in 0.1 M MES buffer, pH 6.8, 1 mM EGTA, 0.1 mM EDTA, 0.5 mM $MgCl_2$, 1 mM DTT, 0.1 mM GTP, 1 mg/mL leupeptin, 1 mg/mL aprotinin, and 100 mg/mL sucrose as stabilizer. The reconstituted tubulin was incubated at 37° C. for 30 min in the presence of 10 mM Peloruside A or 10 mM paclitaxel. Samples (2 mL) were pipetted onto 400-mesh carbon- and Formvar-coated copper grids and left for 2 min at RT before blotting with filter paper. Each grid was stained with 5 mL of 1% uranyl acetate for 3 min at RT, then blotted with filter paper. Grids were air-dried overnight before examination in a Philips CM100 transmission electron microscope.

Figure 6:
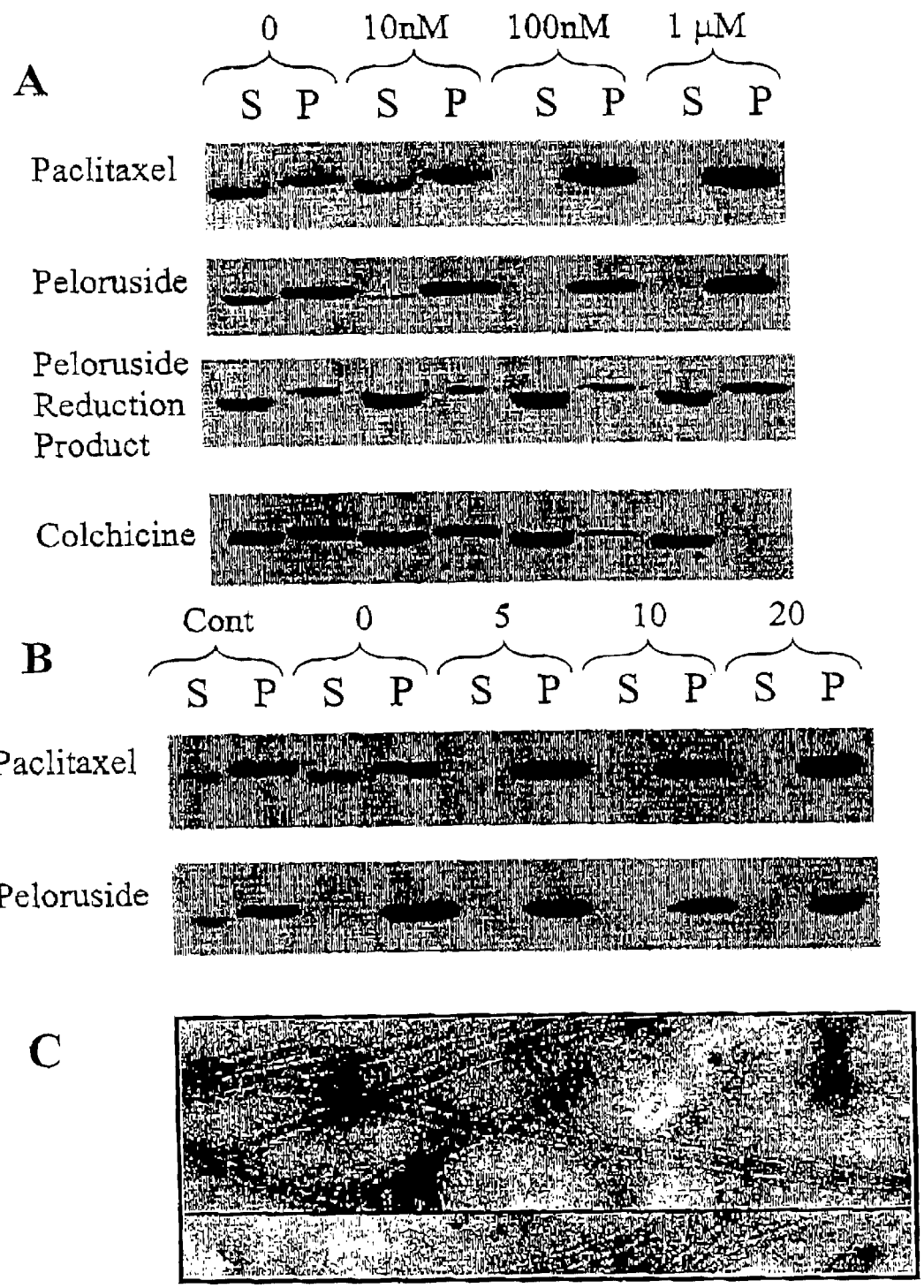
FIG. 6 shows for HL-60 cells immunoblotting for different concentrations of Peloruside, paclitaxel, the $NaBH_4$ reduction product of Peloruside, and colchicine

FIG. 6 shows Peloruside A-induced tubulin polymerization: (A) Immunoblots of b-tubulin following electrophoresis of soluble (S) and particulate (P) fractions of HL-60 cells treated with different concentrations of drug for 5 h. (B) Immunoblots following exposure to 1 mM Peloruside A and 1 mM paclitaxel for varying lengths of time. (C) Transmission electron micrograph of microtubules formed following treatment of purified soluble tubulin with 10 mM Peloruside A for 30 min at 37° C. Scale bar (lower right)=500 nm.

B. Results

Chemical Structures

Figure 3:
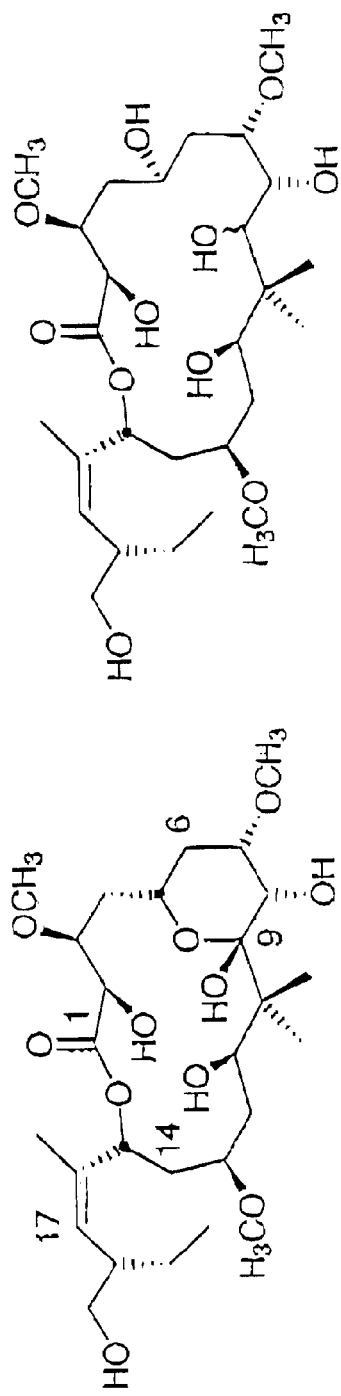
FIG. 3 shows the structures of Peloruside A, the $NaBH_4$ reduction product of Peloruside A, Epothilone A, Laulimalide and Paclitaxel.
Figure 3:
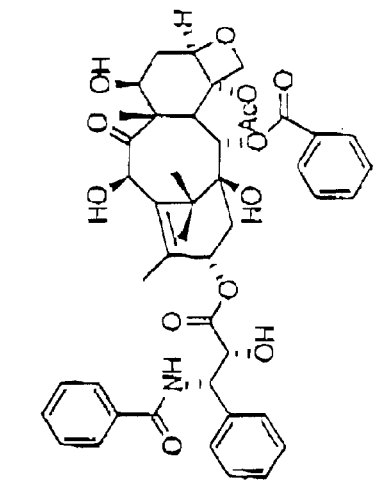
Figure 3:
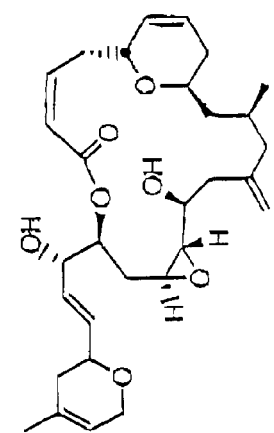
Figure 3:
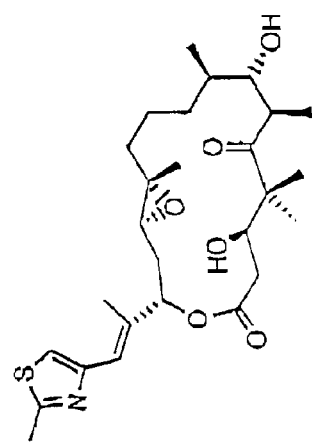

The macrolide ring structures of Peloruside A, paclitaxel, epothilone B, and laulimalide are compared in FIG. 3, along with the structure of the reduction product of Peloruside A in which the 6-membered pyranose ring is opened by chemical reduction, generating a secondary alcohol at $C_9$.

Cytotoxicity $IC_{50}$ values following a 4-day exposure to Peloruside A ranged from 4–15 nM in the different cell lines. No clear differences in MTT response were observed between tumorigenic cell lines (H441, SY5Y, HL-60, 32D-ras) and non-tumorigenic cell lines (32D, LLC-$PK_1$). The $IC_{50}$ values for Peloruside A (7±4 (S.E.M.) nM) and paclitaxel (22±8) were similar in HL-60 cells. Reduction of Peloruside A with $NaBH_4$ increased its $IC_{50}$ value 31-fold in HL-60 cells (221±24 nM).

Cellular Morphology

After 2 days exposure to 100 nM Peloruside A or paclitaxel, multiple micronuclei were observed in H441 cells (FIGS. 4B, C) and K562 cells (data not presented). Longer exposures increased the number of micronuclei and the number of cells containing micronuclei. The center of the micronuclei stained strongly with PI, indicating double-stranded DNA was present (data not presented). In both Peloruside A- and paclitaxel-treated H441 cells, large intracellular fiber bundles were observed by phase-contrast microscopy (FIGS. 4B, C).

Anti-inflammatory and Metabolic Activity

Peloruside A and paclitaxel were tested for their ability to inhibit the fMLP-activated respiratory burst of human neutrophils in vitro. At high concentrations of Peloruside A (26 mM), 26% inhibition of superoxide production was observed whereas paclitaxel (12 mM) had no effect on neutrophil activation. In a similar short-term assay that measures metabolic activity in proliferating cells, Peloruside A at 180 mM stimulated WST-1 reduction by 20%, rather than inhibiting as might be expected for a potent cytotoxic agent. In this assay, paclitaxel inhibited WST-1 reduction by 70% at 120 mM but had little effect at 12–24 mM.

Cell Cycle Arrest

Treatment of H441 cells with 1 mM Peloruside A or paclitaxel for 24 h led to partial cell cycle arrest at $G_2$/M (FIG. 5). The progression of cells into apoptosis/necrosis was seen as an increase in the number of cells in the subdiploid peak. The arrest in $G_2$/M was more complete for paclitaxel than for Peloruside A, and this difference was mirrored in the mitotic index of the cultures. Cells treated with 1 mM Peloruside A had 34±2% metaphase-arrested cells whereas 64±4% of cells showed metaphase arrest following paclitaxel treatment. Control H441 cultures without drug typically had about 4% cells in mitosis (FIG. 5).

Tubulin Polymerization

Tubulin in soluble and particulate fractions from HL-60 cells exposed to different concentrations of Peloruside A, paclitaxel, Peloruside A reduction product, or colchicine for 5 h were isolated and visualized by immunoblotting for b-tubulin (FIG. 6A). Peloruside A and paclitaxel caused similar, dose-dependent shifts of soluble tubulin to the particulate fraction. No detectable b-tubulin remained in the soluble fraction at 100 nM of either drug. Peloruside A reduction product had no significant effect on the proportion of soluble to polymerized tubulin in HL-60 cells. Colchicine, as expected, caused depolymerization of tubulin, with most of the tubulin in the soluble fraction at 1 mM concentration of drug.

A 20 min time course was carried out in the presence of 1 mM Peloruside A and 1 mM paclitaxel (FIG. 6B). By 5 min, both Peloruside A and paclitaxel had converted almost all detectable tubulin to the polymerized form.

10 mM Peloruside A, like paclitaxel, caused purified tubulin to polymerize in solution into typical, long, straight microtubules at 37° C. (FIG. 6C). In the absence of drug, only a few sparse microtubules were seen by electron microscopy. Once formed, the microtubules induced by Peloruside A and paclitaxel were stable at 0C.

C. Discussion

Peloruside A alters microtubule dynamics in a manner similar to that reported for paclitaxel by inducing tubulin polymerization in situ and in cell-free systems, causing cells to arrest in the $G_2$/M phase of the cell cycle. Despite the similarity of the primary mode of action of Peloruside A to the taxanes, epothilones, and laulimalides, the structure and some bioactivities of Peloruside A are unique, including its anti-inflammatory activity and its possible enhancing effects on cell metabolism. In addition, Peloruside A was less effective than paclitaxel at causing mitotic arrest in H441 cells. These unique properties present novel benefits for anti-cancer targeting. Based on thin layer chromatography results, Peloruside A is less lipophilic than paclitaxel, and this property should aid the clinical application of Peloruside A or its analogues, since some of the side-effects of paclitaxel relate to its low aqueous solubility (6–11 mM) (Ter Haar E. et al.). Discodermolide is estimated to be 160-fold more soluble than paclitaxel, based on an indirect, fragment-based computational calculation (Ter Haar E. et al.). Laulimalides presumably have low aqueous solubility since they were selected in part on the basis of their lipophilic properties (He L. et al. and Mooberry S. L. et al.).

Peloruside A induced the formation of multiple micronuclei, intracellular bundles, and metaphase arrest in a manner similar to paclitaxel, epothilone, and laulimalide. Cell-type specific differences exist in the reported responses to paclitaxel, since some cells, such as HL-60 and the colon carcinoma cell line HT-29 arrest in metaphase, then undergo apoptosis, whereas other cells, such as K562 and the melanoma cell line SK-MEL-28, progress through metaphase and become polyploid in the presence of drug (Banerjee S., Fallis A. G., Brown D. L., *Oncol. Res.* (1997), 9, 237–248 and Roberts J. R., Allison D. C., Donehower R. C., Rowinsky E. K., *Cancer Res.* (1990), 50, 710–716). The apoptosis induced by Peloruside A (Hood K. A. et al.) is presumed to be a consequence of $G_2$/M block or the DNA damage due to abnormal mitotic arrest. Mitotic arrest often induces apoptosis in cultured cells (Bollag D. M. et al., and Wang T. H., Wang H. S., Soong Y. K., *Cancer* (2000), 88, 2619–2628). With epothilone and paclitaxel, endonucleolytic cleavage of DNA, measured by the TUNEL assay, is only seen in $G_2$/M-blocked cells (Bollag D. M. et al, and Wang T. H. et al). The apoptotic pathway for paclitaxel has been directly examined.

The evidence that Peloruside A is a microtubule-stabilizing agent is based on an in situ cell assay (FIGS. 6A, B) and an in vitro polymerization assay (FIG. 6C) in which a shift in tubulin from a soluble to a particulate form was observed. This conclusion that Peloruside A stabilizes microtubules in a manner similar to the taxanes and other microtubule-stabilizing drugs is also supported by the $G_2$/M cell cycle arrest data of FIG. 5. More direct measurements of Peloruside A-tubulin interactions in cell-free systems will be needed to fully describe the primary mode of action of Peloruside A, and these experiments are in progress.

Peloruside A is a novel natural product which, together with its functionally equivalent analogues, has paclitaxel-like microtubule-stabilizing activity. Peloruside A and its functionally equivalent analogues represent new drugs in an elite group of drugs of major importance in the clinical treatment of solid tumors. Pelorutide A is structurally distinct and may present a unique profile of bioactivity that will add to that of the limited number of other known microtubule-stabilizing drugs available for development.

INDUSTRIAL APPLICATION

Thus, in accordance with the present invention, the applicants provide a new bioactive compound, and its functionally equivalent analogues, which have cytotoxic properties. These compounds can be formulated into medicaments, including pharmaceutical compositions, for use in any prophylactic or therapeutic application for which their cytotoxic properties make them appropriate. Such therapeutic applications include anti-tumor treatment.

Those persons skilled in the art will appreciate that the above description is provided by way of example only and that variations and modifications can be made without departing from the scope of the invention which has been made.

What is claimed is:

1. A compound of formula (I');

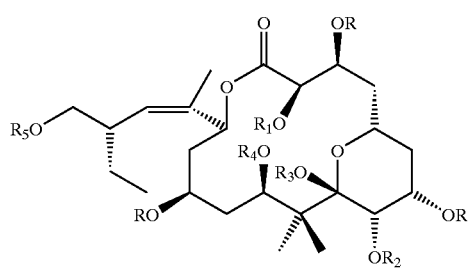

wherein each of $R_1$, $R_2$, $R_3$, $R_4$ and $R_5$ is, independently, hydrogen, alkyl or acyl; and each R is, independently, hydrogen or alkyl; or a compound of formula (II');

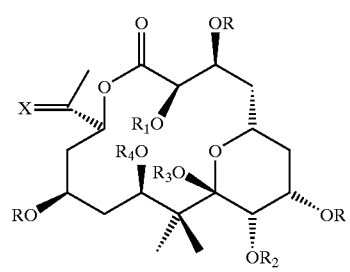

wherein X is O or $=C(R_6)R_7$;

each of $R_1$, $R_2$, $R_3$, $R_4$, $R_5$, $R_6$ and $R_7$ is, independently, hydrogen, alkyl or acyl; and each R is, independently, hydrogen or alkyl.

2. A compound of claim 1 of formula (I);

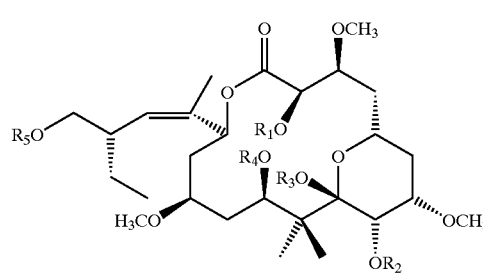

wherein each of $R_1$, $R_2$, $R_3$, $R_4$ and $R_5$ is, independently, hydrogen, alkyl or acyl; or a compound of formula (II);

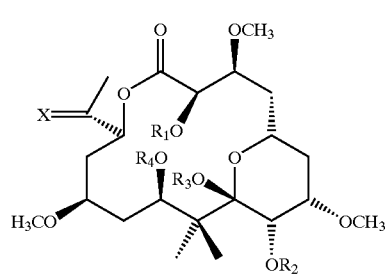

wherein X is O or $=C(R_6)R_7$; and each $R_1$, $R_2$, $R_3$, $R_4$, $R_5$, $R_6$ and $R_7$ is, independently, hydrogen, alkyl or acyl.

3. A compound of formula (I') as defined in claim 1.
4. A compound of formula (II') as defined in claim 1.
5. A compound according to claim 2 of formula (III)

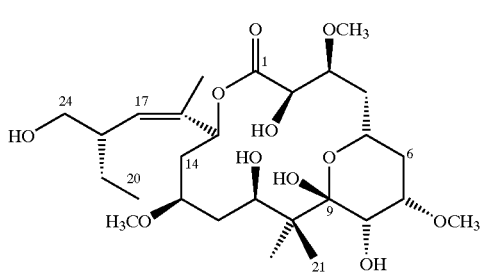

6. A compound of formula (IV)

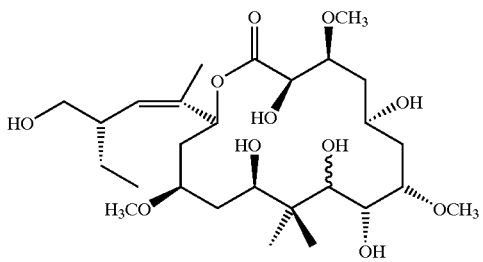

(IV)

7. A composition which comprises a compound of formula (I') or formula (II') as defined in claim 1, together with a suitable carrier therefor.

8. A pharmaceutical composition which comprises a compound of formula (I) or formula (II) as defined in claim 2, together with a pharmaceutically-acceptable carrier therefor.

9. A pharmaceutical composition which comprises a compound of formula (III) as defined in claim 5, together with a pharmaceutically-acceptable carrier therefor.

10. A pharmaceutical composition according to claim 9 wherein the compound is of formula (III).

11. A method of prophylaxis or therapy, wherein the prophylaxis or therapy is achieved by inhibiting the proliferation of cells, which comprises the step of administering to a mammal in need of same a compound of formula (I') or formula (II') as defined in claim 1.

12. The method of claim 11 wherein the cells are tumor cells.

13. The method of claim 11 wherein the compound is administered in an amount effective to provide microtubule stabilization.

14. A method of prophylaxis or therapy, wherein the prophylaxis or therapy is achieved by inhibiting the proliferation of cells, which comprises the step of administering to a mammal in need of same a compound of formula (III) as defined in claim 5.

15. The method of claim 14 wherein the cells are tumor cells.

16. The method of claim 14 wherein the compound is administered in an amount effective to provide microtubule stabilization.

17. A method of prophylaxis or therapy, wherein the prophylaxis or therapy is achieved by inhibiting the proliferation of cells, which comprises the step of administering to a patient in need of same a composition according to claim 7.

18. A method of prophylaxis or therapy, wherein the prophylaxis or therapy is achieved by inhibiting the proliferation of cells, which comprises the step of administering to a patient in need of same a pharmaceutical composition according to claim 8.

19. A method of prophylaxis or therapy, wherein the prophylaxis or therapy is achieved by inhibiting the proliferation of cells, which comprises the step of administering to a patient in need of same a pharmaceutical composition according to claim 9.

20. A method of prophylaxis or therapy, wherein the prophylaxis or therapy is achieved by inhibiting the proliferation of cells, which comprises the step of administering to a patient in need of same a pharmaceutical composition according to claim 10.

* * * * *